United States Patent
Koo et al.

(10) Patent No.: US 11,192,090 B2
(45) Date of Patent: Dec. 7, 2021

(54) ALCOHOL DEHYDRATION CATALYST, PREPARATION METHOD THE SAME AND METHOD FOR PREPARING ALPHA-OLEFINS USING THE SAME

(71) Applicant: KOREA INSTITUTE OF ENERGY RESEARCH, Daejeon (KR)

(72) Inventors: Kee Young Koo, Daejeon (KR); Un-ho Jung, Daejeon (KR); Young-eun Kim, Jeju-si (KR); Hyo Been Im, Daejeon (KR); Dong Hyun Chun, Daejeon (KR); Min Hye Youn, Sejong-si (KR); Heon-do Jeong, Daejeon (KR); Ji-chan Park, Daejeon (KR); Geun Bae Rhim, Daejeon (KR); Dong-wook Lee, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 1 day.

(21) Appl. No.: 16/791,392

(22) Filed: Feb. 14, 2020

(65) Prior Publication Data
US 2020/0306732 A1    Oct. 1, 2020

(30) Foreign Application Priority Data

Mar. 25, 2019  (KR) .................. 10-2019-0033666
Jan. 23, 2020  (KR) .................. 10-2020-0009292

(51) Int. Cl.
*B01J 23/30*   (2006.01)
*B01J 21/10*   (2006.01)
(Continued)

(52) U.S. Cl.
CPC .............. *B01J 23/30* (2013.01); *B01J 21/10* (2013.01); *B01J 27/236* (2013.01);
(Continued)

(58) Field of Classification Search
CPC . B01J 23/30; B01J 21/10; B01J 27/236; B01J 37/0201; B01J 37/088; B01J 23/005;
(Continued)

(56) References Cited

U.S. PATENT DOCUMENTS

2008/0287722 A1    11/2008  Dierker
2010/0275509 A1*   11/2010  Sakuma .................. B01J 25/02
                                              44/438
(Continued)

FOREIGN PATENT DOCUMENTS

CN         105312044 A      2/2016
KR    10-2007-0112460 A    11/2007

OTHER PUBLICATIONS

Di Cosimo et al., "Structural Requirements and Reaction Pathways in Condensation Reactions of Alcohols on Mg,AlO, Catalysts," Journal of Catalysts (2000), vol. 190, pp. 261-275.

(Continued)

*Primary Examiner* — Ali Z Fadhel
(74) *Attorney, Agent, or Firm* — Birch, Stewart, Kolasch & Birch, LLP

(57) ABSTRACT

The present invention relates to a catalyst for dehydration of a primary alcohol, a method of preparing the same, and a method of producing an alpha-olefin using the same. The catalyst for dehydration of a primary alcohol according to the present invention has an excellent catalyst stability while having an excellent activity with respect to dehydration, and a high turnover frequency, such that a linear alpha-olefin with high purity may be produced with a high selectivity even in a case where a relatively small amount of a cocatalyst is added as compared with a homogeneous catalyst system.

12 Claims, 1 Drawing Sheet

(51) Int. Cl.
    *B01J 27/236*     (2006.01)
    *B01J 37/02*     (2006.01)
    *C07C 1/24*     (2006.01)
    *B01J 37/08*     (2006.01)

(52) U.S. Cl.
    CPC ......... *B01J 37/0201* (2013.01); *B01J 37/088* (2013.01); *C07C 1/24* (2013.01); *C07C 2521/02* (2013.01); *C07C 2521/10* (2013.01); *C07C 2523/30* (2013.01)

(58) Field of Classification Search
    CPC ... C07C 1/24; C07C 2523/30; C07C 2521/10; C07C 2521/02
    See application file for complete search history.

(56) References Cited

U.S. PATENT DOCUMENTS

| | | | | |
|---|---|---|---|---|
| 2010/0298133 | A1* | 11/2010 | Takahashi | B01J 37/0009 502/341 |
| 2013/0245348 | A1* | 9/2013 | Vermeiren | C07C 6/04 585/324 |
| 2014/0171693 | A1* | 6/2014 | Zhang | B01J 23/78 568/902.2 |
| 2018/0257063 | A1* | 9/2018 | Choi | B01J 27/188 |

OTHER PUBLICATIONS

Macht et al., "Support effects on Bronsted acid cite densities and alcohol dehydration turnover rates on tungsten oxide domains," Journal of Catalysts (2004), vol. 227, pp. 479-491.

\* cited by examiner

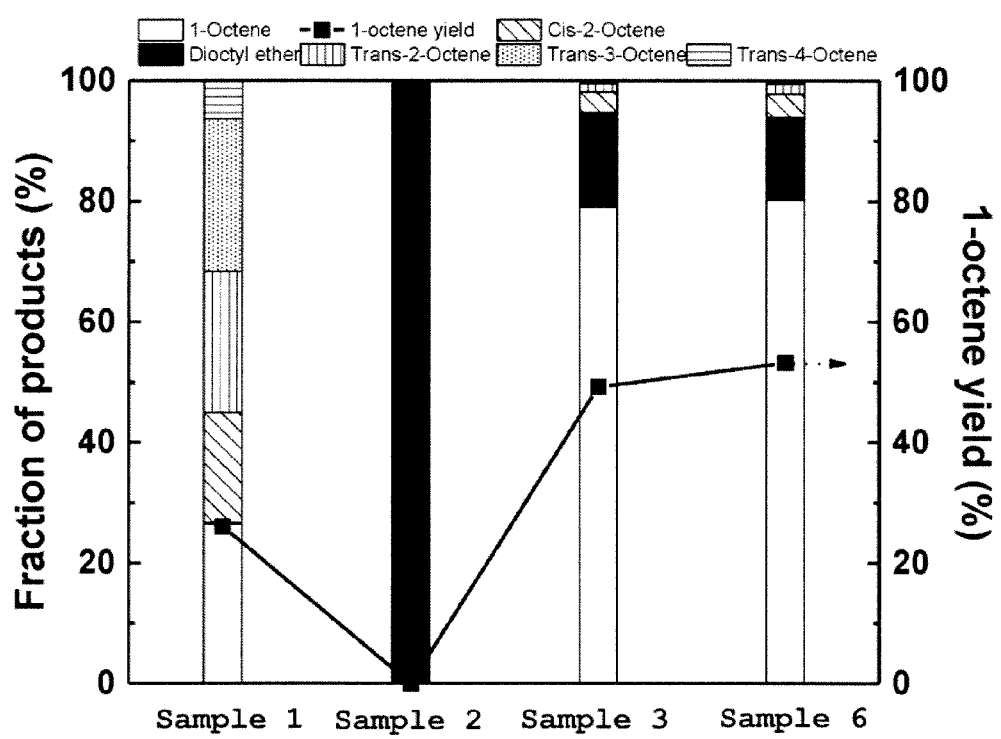

ALCOHOL DEHYDRATION CATALYST, PREPARATION METHOD THE SAME AND METHOD FOR PREPARING ALPHA-OLEFINS USING THE SAME

CROSS-REFERENCE TO RELATED APPLICATIONS

This application claims priority under 35 U.S.C. § 119 to Korean Patent Application No. 10-2019-0033666 and 10-2020-0009292, filed on Mar. 25, 2019, and Jan. 23, 2020 in the Korean Intellectual Property Office, the disclosure of which is incorporated herein by reference in its entirety.

TECHNICAL FIELD

The following disclosure relates to a catalyst for dehydration of an alcohol, a method of preparing the same, and a method of producing an alpha-olefin using the same.

BACKGROUND

A linear alpha-olefin having 4 to 20 carbon atoms is important feedstock in the production of a surfactant, a plasticizer, a synthetic lubricant, and a polyolefin. In addition, a linear alpha-olefin with high purity is particularly valuable in the production of low-density polyethylene and in an oxo process.

A linear olefin may be produced by dehydrogenation of a linear alkane or dehydration of a linear alcohol. However, the major portion of products thus obtained by the production method consists of an internal olefin. Therefore, studies have been continuously conducted to produce a linear alpha-olefin with a higher selectivity.

Among various linear alpha-olefins, 1-butene, 1-hexene, or 1-octene serves an important role in a change in physical properties of a polymer, as a comonomer to be polymerized into low-density polyethylene (LDPE) and high-density polyethylene (HDPE) by polymerization with ethylene. Polyethylene, which is a thermoplastic plastic, is light and flexible, and thus has been used in various containers, a film for packaging, a fiber, a pipe, packing, and a paint, in modern society. In the case of polyethylene, important demand properties of a polymer, such as a breaking strength, a tearing strength, and a dart impact strength, are influenced by properties of a polymer, such as crystallization and crosslink density. That is, the important demand properties of polyethylene may be adjusted by a combination of various types of linear alpha-olefins which are comonomers.

As a commercial process of producing a linear alpha-olefin, there are a method of producing an alpha-olefin by oligomerization of ethylene, and a method of separating olefins through cracking of naphtha from crude oil and producing an alpha-olefin. However, in the commercial process of producing a linear alpha-olefin, unit costs rise and environmental problems occur in the separation step. Accordingly, there is a need for a commercial process of producing a linear alpha-olefin through dehydration by using an alcohol converted from biomass that is an environmentally friendly carbon resource that is renewable and sustainably producible.

RELATED ART DOCUMENT

Patent Document (Patent Document 1) KR 10-2007-0112460 A

SUMMARY

An embodiment of the present invention is directed to providing a catalyst to be effectively used in dehydration of a primary alcohol and a method of preparing the same.

Specifically, the embodiment of the present invention is directed to providing a catalyst for dehydration of a primary alcohol, the catalyst having an excellent activity with respect to dehydration, a high turnover frequency, and an excellent catalyst stability, and a method of preparing the same.

Specifically, the embodiment of the present invention is directed to providing a catalyst for dehydration of a primary alcohol, the catalyst capable of implementing production of a linear alpha-olefin with high purity by implementing high catalytic activity and a high selectivity for a linear alpha-olefin through dehydration even with an addition of a relatively small amount of a cocatalyst as compared with a homogeneous catalyst system, and a method of preparing the same.

Another embodiment of the present invention is directed to providing a method of converting a primary alcohol into an olefin with a high selectivity by using the catalyst for dehydration of a primary alcohol.

Still another embodiment of the present invention is directed to providing a method of mass-producing a linear alpha-olefin in a very cost-efficient manner.

In one general aspect, a catalyst for dehydration of a primary alcohol includes a composite metal oxide of magnesium (Mg) and aluminum (Al).

The composite metal oxide may be selected from magnesium aluminate ($MgAl_2O_4$) and hydrotalcite ($Mg_{2x}Al_2(OH)_{4x+4}CO_3 \cdot nH_2O$).

The composite metal oxide may be used as a carrier, and the catalyst for dehydration of a primary alcohol may further include metal particles supported on the carrier.

The metal particles may be selected from an alkaline earth metal and a transition metal.

The metal particles may be formed of tungsten (W).

The metal particles may be supported in an amount of 10 wt % or less with respect to a total weight of the carrier.

The primary alcohol may be 1-octanol.

In another general aspect, a method of preparing a catalyst for dehydration of a primary alcohol includes: preparing a metal supported material by supporting a metal precursor solution on a composite metal oxide of magnesium (Mg) and aluminum (Al) by an impregnation method; and calcining the support material.

A metal precursor of the metal precursor solution may be an ammonium-based compound including a metal selected from an alkaline earth metal and a transition metal.

The metal precursor may be an ammonium-based tungsten compound selected from ammonium paratungstate and ammonium metatungstate.

In still another general aspect, there is provided a method of converting a primary alcohol into an olefin using the catalyst for dehydration of a primary alcohol.

In still another general aspect, a method of producing a linear alpha-olefin includes: converting a primary alcohol into an olefin using the catalyst for dehydration of a primary alcohol; and fractionating the converted olefin.

The converting may be performed at 200 to 800° C.

In the converting, the primary alcohol may be fed at a liquid hourly space velocity (LHSV) of 3 to 100 $h^{-1}$.

The fractionating may be performed by distillation, extraction, adsorption, or ion exchange.

A conversion ratio of the primary alcohol may be 50% or more, and a selectivity for the linear alpha-olefin may be 60% or more.

Other features and aspects will be apparent from the following detailed description, the drawings, and the claims.

BRIEF DESCRIPTION OF THE DRAWINGS

FIG. 1 is a graph illustrating the results of products produced by dehydration of a primary alcohol using catalysts or catalyst systems of Examples and Comparative Examples of the present invention (Sample 1: Comparative Example 5, Sample 2: Comparative Example 4, Sample 3: Example 15, and Sample 6: Example 16).

DETAILED DESCRIPTION OF EMBODIMENTS

Hereinafter, a catalyst for dehydration of an alcohol, a method of preparing the same, and a method of producing an alpha-olefin using the same, according to the present invention will be described. However, technical terms and scientific terms used herein have the general meaning understood by those skilled in the art to which the present invention pertains unless otherwise defined, and a description for the known function and configuration obscuring the present invention will be omitted in the following description.

The term "comprising" used herein is an open-ended description that is synonymous with an expression such as "including," "containing," "having", or "characterized by," and does not exclude additionally unenumerated elements, materials, or steps.

The term "primary alcohol" used herein refers to an alcohol having an alcohol group (—OH) bonded to a terminal thereof. Specifically, the primary alcohol may be an alcohol having 20 or fewer carbon atoms, more specifically, an alcohol having 6 to 20 carbon atoms, and most preferably, 1-octanol which is an alcohol having 8 carbon atoms.

The term "linear alpha-olefin" used herein refers to a hydrocarbon compound in which carbon 1 and carbon 2 of a hydrocarbon are double bonded, and examples thereof may include 1-hexene and 1-octene.

The term "dehydration" used herein refers to a reaction in which water is removed from the primary alcohol, and a product produced by the reaction may be an olefin, an ether, or the like.

The term "catalyst" used herein has the same meaning as a catalyst for dehydration of a primary alcohol. In addition, examples of the catalyst may include a catalyst having several Lewis acid sites, and a catalyst supporting a cocatalyst or the like.

Singular forms used herein may be intended to include plural forms unless otherwise interpreted in context.

Unless otherwise particularly stated, units used herein are based on a weight. As an example, a unit of "%" or "ratio" refers to "wt %" or "weight ratio", respectively, and "wt %" means wt % of any one component in the total components unless otherwise defined.

A numerical range used herein includes all possible combinations of lower and upper limit values and all values in a range thereof, an increment logically derived from the type and width of a defined range, all values limited among the values, and lower and upper limit values in numerical ranges limited by different types from each other.

As described above, in a case where dehydration is performed using a primary alcohol, an olefin or an ether is produced. Specifically, a reaction by which an olefin is produced may be represented by the following Reaction Formula 1, and a reaction by which an ether is produced may be represented by the following Reaction Formula 2.

$ROH \rightarrow CH_2=CH-R'+H_2O$     [Reaction Formula 1]

$2R''OH \rightarrow R''-O-R''+H_2O$     [Reaction Formula 2]

[In Reaction Formulas 1 and 2,

R is $C_2$-$C_{20}$alkyl,

R' is hydrogen or $C_1$-$C_{18}$alkyl, and

R'' is $C_1$-$C_{20}$alkyl.]

The dehydration as shown in Reaction Formula 1 is an endothermic reaction by which an olefin is produced through the removal of water by a catalyst. In addition, the dehydration as shown in Reaction Formula 2 is an exothermic reaction by which a dialkyl ether is produced from a reaction of two molecules of a primary alcohol.

As such, it is important to adjust a catalyst, a composition thereof, and a reaction condition in order to produce an olefin from a primary alcohol with a high selectivity.

As a result of repeatedly conducting studies to produce an olefin from dehydration of a primary alcohol with a high selectivity, the inventors of the present invention found that, in a case where a composite metal oxide containing both magnesium (Mg) and aluminum (Al) is used as a catalyst, a side reaction may be suppressed, and a linear alpha-olefin may be produced with a high selectivity, thereby suggesting the present invention.

According to the present invention, it is possible to produce a linear alpha-olefin with high purity which is valuable in the production of a high value-added low-density polyethylene and in an oxo process by a very cost-efficient method by using an alcohol converted from biomass that is an environmentally friendly carbon resource that is renewable and sustainably producible.

In addition, according to the present invention, it is possible to implement a desired catalytic activity with respect to dehydration by an endothermic reaction, that is, an excellent turnover frequency. Further, in a case where the catalyst is used as a carrier and a cocatalyst is supported thereon, acidity of the catalyst is increased, and Lewis acid site (LAS) of the catalyst is controlled to have several sites, such that dehydration characteristics further improved may be implemented. The improvement of specific dehydration characteristics will be described below.

In addition, according to the present invention, high catalytic activity may be implemented, and both a high selectivity and yield may be implemented by controlling a Lewis acid site that serves as an active site in dehydration of a primary alcohol and effectively reducing production of isomers, even in a case where a relatively small amount of a cocatalyst is added as compared with a homogeneous catalyst system.

Hereinafter, the present invention will be described in detail.

In order to implement the objects and effects described above, the present invention provides a catalyst for dehydration of a primary alcohol, the catalyst including: a composite metal oxide of magnesium (Mg) and aluminum (Al). Specifically, the composite metal oxide is distinguished from a metal oxide in which magnesium oxide and aluminum oxide are mixed.

The catalyst for dehydration of a primary alcohol according to an exemplary embodiment of the present invention may include a composite metal oxide selected from magnesium aluminate ($MgAl_2O_4$), hydrotalcite ($Mg_2$—$Al_2(OH)_{4x+4}CO_3.nH_2O$), and the like.

The above-mentioned composite metal oxide has a very dense structure in which magnesium and aluminum are uniformly bonded to each other while forming a layer structure at a ratio of a relatively wide range at an atomic level. Therefore, dispersibilities and uniformities of magnesium and aluminum are very high.

In a case where the catalyst for dehydration of a primary alcohol is used, both extremely improved selectivity and yield are implemented as compared to a case where magnesium oxide or aluminum oxide is used alone. Further, when taking into consideration that, in a case where magnesium oxide and aluminum oxide are physically mixed and used, reaction by-products such as internal olefins are excessively produced, such that a linear alpha-olefin with high purity may not be produced, and it may be expected that the objects and effects according to the present invention result from the structural features of the catalyst including both magnesium and aluminum.

As an example, in a case where aluminum oxide having a relatively high Lewis acid site intensity is used as a catalyst, a conversion ratio of the primary alcohol may be high, but various types of isomers including internal olefins are simultaneously produced, a selectivity and a yield with respect to a linear alpha-olefin are thus significantly reduced.

As an example, in a case where magnesium oxide having a relatively low Lewis acid site intensity is used as a catalyst, only a linear alpha-olefin and a dialkyl ether are obtained, such that a linear alpha-olefin with high purity may be produced; however, a selectivity and a yield with respect to a linear alpha-olefin are significantly reduced.

On the other hand, the catalyst for dehydration of a primary alcohol includes a composite metal oxide selected from magnesium aluminate ($MgAl_2O_4$), hydrotalcite ($Mg_{2x}Al_2(OH)_{4x+4}CO_3.nH_2O$), and the like, such that both extremely improved selectivity and yield with respect to a linear alpha-olefin may be implemented, and purity of the thus-obtained linear alpha-olefin may also be increased, which is preferable.

As an example, the magnesium aluminate may be a commercial magnesium aluminate, or may be magnesium aluminate prepared by calcining commercial hydrotalcite ($Mg_{2x}Al_2(OH)_{4x+4}CO_3.nH_2O$) at a temperature of 500 to 1,100° C. in an air atmosphere.

As an example, the magnesium aluminate may contain 10 to 300 parts by weight of alumina (aluminum oxide, $Al_2O_3$) with respect to 100 parts by weight of magnesium oxide (MgO). Specifically, the magnesium aluminate may contain magnesium oxide (MgO) and alumina ($Al_2O_3$) at a weight ratio (MgO:$Al_2O_3$) of 30:70, 50:50, or 70:30.

As an example, in order to further improve a conversion ratio of a primary alcohol and a selectivity for a linear alpha-olefin, a weight ratio of magnesium oxide in the magnesium aluminate may be adequately adjusted.

As an example, the hydrotalcite may be a commercial hydrotalcite ($Mg_6Al_2(CO_3)(OH)_{16}.4H_2O$) or the like, but is not limited thereto.

In the catalyst for dehydration of a primary alcohol according to an exemplary embodiment of the present invention, the composite metal oxide may be used as a carrier, and metal particles supported on the carrier may be included, in order to implement a desired Lewis acid site depending on a reactant. In this case, the metal particles serve as a cocatalyst.

The metal particles may be selected from an alkaline earth metal, a transition metal, and the like.

As an example, the metal particles may be formed of one or two or more selected from an alkaline earth metal such as beryllium (Be), magnesium (Mg), calcium (Ca), strontium (Sr), barium (Ba), or radium (Ra); and a transition metal such as niobium (Nb), zinc (Zn), cerium (Ce), zirconium (Zr), iron (Fe), molybdenum (Mo), or tungsten (W).

In the catalyst for dehydration of a primary alcohol according to an exemplary embodiment of the present invention, specifically, the metal particles may be formed of a Group 6 transition metal selected from molybdenum (Mo) and tungsten (W), and more specifically, the metal particles may be formed of tungsten (W).

As an example, the metal particles may have an average particle diameter (D50) or more at an atomic level. Specifically, the average particle diameter of the metal particles may be 2 to 10 nm, and more specifically, 3 to 5 nm. In this case, the average particle diameter means a value of a diameter corresponding to 50% from the smallest particle side when the total number of particles is 100%. D50 may be measured by a method well-known to those skilled in the art. As an example, D50 may be measured by a particle size analyzer, or may be measured from a TEM photograph or an SEM photograph.

As an example, the metal particles may be uniformly distributed on a surface of the carrier or in pores of the carrier. In this case, the metal particles may be distributed on the surface of the carrier or in the pores of the carrier in a supported manner.

As an example, the metal particles may be supported in an amount of 10 wt % or less with respect to the total weight of the carrier. A supported amount of metal particles may be specifically 0.1 to 10 wt %, more specifically 1.0 to 7.5 wt %, and most specifically 4.0 to 6.0 wt %.

As an example, in a case where the catalyst for dehydration of a primary alcohol includes 4.0 to 6.0 wt % of the metal particles, it is preferable in that the conversion ratio of the primary alcohol may be extremely improved and the linear alpha-olefin further improved may be produced. Specifically, in this case, the conversion ratio of the primary alcohol may be 80% or more.

As an example, the primary alcohol may be a linear or branched alcohol.

As an example, the primary alcohol may be a $C_6$-$C_{20}$ alcohol, and non-limiting examples thereof may include hexanol, heptanol, octanol, nonanol, decanol, and undecanol.

As an example, the primary alcohol may be most preferably 1-hexanol or 1-octanol.

The catalyst for dehydration of a primary alcohol according to the present invention may be prepared by a preparation method including: preparing a metal supported material by supporting a metal precursor solution on a composite metal oxide of magnesium (Mg) and aluminum (Al) by an impregnation method; and calcining the support material.

As an example, the calcining may be performed in a gas atmosphere including one or two or more types of gas selected from hydrogen, air, oxygen, and an inert gas. In addition, compositions of the metal particles to be supported may be adjusted depending on a gas atmosphere in the calcining.

As an example, the calcining may be performed at 200 to 800° C. for 3 to 6 hours.

As an example, the preparation method may further include drying the support material at 80 to 110° C. for 6 to 18 hours before the calcining.

In addition, a metal precursor of the metal precursor solution may be an ammonium-based compound including a metal selected from an alkaline earth metal and a transition metal. Non-limiting examples of the ammonium-based compound may include an ammonium-based tungsten compound selected from ammonium paratungstate and ammonium metatungstate, but are not limited thereto.

The catalyst for dehydration of a primary alcohol according to the present invention may include 10 wt % or less of the metal particles with respect to the total weight of the carrier. It is a matter of course that the supported amount of the metal particles may be adjusted in wide ranges depending on a purpose.

As an example, in a case where the catalyst for dehydration of a primary alcohol includes 4 to 6 wt % of the metal particles, a conversion ratio of 1-octanol may be 80% or more. In addition, in this case, the production of reaction by-products is effectively suppressed, such that a linear alpha-olefin with high purity may be produced with a high yield, which is preferable.

Hereinafter, use of the catalyst for dehydration of a primary alcohol according to the present invention will be described.

An aspect of the use according to the present invention may be a method of converting a primary alcohol into an olefin. In addition, an aspect of the use according to the present invention may be a method of producing a linear alpha-olefin, the method including a method of converting a primary alcohol into an olefin.

The method of converting a primary alcohol into an olefin according to an exemplary embodiment of the present invention may be performed at 200 to 800° C. In addition, the method of converting a primary alcohol into an olefin may be performed at an atmospheric pressure to 50 barg.

In order to more effectively convert a primary alcohol into an olefin, the catalyst for dehydration of a primary alcohol may be used after being subjected to a pretreatment at 200° C. or higher for 1 to 5 hours. Specifically, the pretreatment may be performed at 200 to 800° C., but the present invention is not limited thereto.

In addition, in the method of converting a primary alcohol into an olefin according to an exemplary embodiment of the present invention, the primary alcohol which is a reactant may be fed in a vaporized state by being preheated at a boiling point (bp) or higher. A temperature condition for the preheating may be specifically 200° C. or higher, more specifically 200 to 500° C., and most specifically 250 to 450° C.

In addition, in the method of converting a primary alcohol into an olefin according to an exemplary embodiment of the present invention, the primary alcohol which is a reactant may be provided in a vaporized state by being preheated under the condition described above, and the reactant may be more easily brought into contact with a catalyst by using a carrier gas.

As an example, any carrier gas may be used without limitation as long as it does not adversely affect conversion of a primary alcohol into an olefin, and non-limiting examples of the carrier gas may include a nitrogen gas, a helium gas, and an argon gas.

As an example, the primary alcohol may be fed at a feeding speed of 20 to 80 mL/min per 0.5 mL of the catalyst.

In addition, a flow rate of the carrier gas may be determined in proportion to a volume of the catalyst, and may also be adjusted under various conditions depending on a purpose.

In addition, in the method of converting a primary alcohol into an olefin according to an exemplary embodiment of the present invention, the primary alcohol may be fed at a liquid hourly space velocity (LHSV) of 3 to 100 $h^{-1}$. The primary alcohol may be fed at a liquid hourly space velocity of specifically 5 to 80 $h^{-1}$, and more specifically 7 to 56 $h^{-1}$.

A product produced by the method of converting a primary alcohol into an olefin according to an exemplary embodiment of the present invention may be a combination selected from a linear alpha-olefin, an internal olefin, a dialkyl ether, and the like.

In the method of converting a primary alcohol into an olefin according to an exemplary embodiment of the present invention, extremely improved selectivity and yield are implemented as compared to a case where a catalyst including only magnesium oxide or aluminum oxide, or a mixture of a metal oxide in which magnesium oxide and aluminum oxide are mixed is used as a catalyst.

Specifically, according to the above method, a conversion ratio of a primary alcohol is equal to or slightly lower than a conversion ratio of a primary alcohol in the case where aluminum oxide having a relatively high Lewis acid site intensity is used as a catalyst, but the production of by-products may be effectively suppressed, and a linear alpha-olefin may be produced with a high selectivity, which is commercially advantageous.

A linear alpha-olefin may be finally obtained by fractionating the converted olefin by a general fraction method.

Any fraction method may be used without limitation as long as it is a general method. Non-limiting examples of the fraction method may include distillation, extraction, adsorption, and ion exchange, and the fractionating may be performed by at least one fraction method selected from distillation, extraction, adsorption, and ion exchange.

In this case, distillation with soxhlet may be preferable in terms of an advantage in a process. However, since the linear alpha-olefin and the internal olefin among the products obtained through the converting of a primary alcohol into an olefin have similar boiling points, it is very difficult to separate the linear alpha-olefin and the internal olefin from each other. Therefore, in the converting of a primary alcohol into an olefin, a high selectivity for a linear alpha-olefin may be a very important factor in the production of a linear alpha-olefin with high purity.

As an example, in a case where 1-octanol (bp of 188° C.) is used as a reactant, the olefin converted from the 1-octanol may be 1-octene (bp of 121° C.), cis-2-octene (bp of 126° C.), trans-2-octene (bp of 123° C.), cis-3-octene (bp of 123° C.), trans-3-octene (bp of 121 to 122° C.), trans-4-octene (bp of 122 to 123° C.), and the like. As mentioned above, since 1-octene which is a desired linear alpha-olefin and a by-product simultaneously produced with 1-octene have similar boiling points, it is very difficult to separate the 1-octene and the by-product from each other.

In the method of producing a linear alpha-olefin according to an exemplary embodiment of the present invention, a conversion ratio of the primary alcohol may be 50% or more.

Specifically, in the method of producing a linear alpha-olefin, the conversion ratio of the primary alcohol may be 50% or more, and the selectivity for the linear alpha-olefin may be 60% or more. More specifically, in the method of producing a linear alpha-olefin, the conversion ratio of the primary alcohol may be 70 to 90%, and the selectivity for the linear alpha-olefin may be 65 to 90%. Most specifically, in the method of producing a linear alpha-olefin, the conversion ratio of the primary alcohol may be 80 to 90%, and the selectivity for the linear alpha-olefin may be 75 to 90%.

In addition, in the method of producing a linear alpha-olefin, a yield of the linear alpha-olefin may be 45% or more.

Hereinafter, the present invention will be described in more detail with reference to Examples and Comparative Examples. However, the following Examples and Comparative Examples are merely provided to describe the present invention in more detail, and are not intended to limit the present invention. Unless otherwise stated in the present invention, all temperatures are in a unit of ° C., and the amounts of compositions used are in a unit of wt %.

(Evaluation Method)

1. Observation of Product Produced by Dehydration

A product obtained from a reactor was converted into a liquid phase in a condenser of −2° C., and a liquid phase product was collected in a separator having a length of 20 cm and a volume of 15 mL. The collected liquid phase product was analyzed by a GC-FID (7890B, Agilent Technologies, Inc.) equipped with an HP-5 column (19091)-413, Agilent Technologies, Inc.). At this time, measurement times of the product were compared based on 3 hours of dehydration.

2. Observation of Dehydration Characteristics

The dehydration characteristics in each of Examples and Comparative Examples according to the present invention were calculated by the following Equations 1 to 4.

Conversion ratio of 1-octanol (%)=(Reacted 1-octanol (Mole))/(Fed 1-octanol (Mole))×100    [Equation 1]

Selectivity for 1-octene (%)=(1-Octanol reacted into 1-octene (Mole))/(Reacted 1-octanol (Mole))×100    [Equation 2]

Yield of 1-octene (%)=(1-Octanol reacted into 1-octene (Mole))/(Fed 1-octanol (Mole))×100    [Equation 3]

Purity of 1-octene (%)=(1-Octene (Mole))/(Total octene (Mole))×100

Total octene=(1-Octene)+(Cis-2-octene)+(Trans-2-octene)+(Trans-3-octene)+(Trans-4-octene)    [Equation 4]

Example 1

Hydrotalcite powder (manufacturer: SASOL GmbH Germany, product name: PURAL® MG30, MgO:Al$_2$O$_3$=30:70 (wt:wt)) was calcined in an oven of 850° C. in an air atmosphere for 3 hours, thereby preparing magnesium aluminate which is a catalyst for dehydration of a primary alcohol.

Example 2

Hydrotalcite powder (manufacturer: SASOL GmbH Germany, product name: PURAL® MG50, MgO:Al$_2$O$_3$=50:50 (wt:wt)) was used. Calcination was performed in the same manner as that of Example 1, thereby preparing magnesium aluminate which is a catalyst for dehydration of a primary alcohol.

Example 3

Hydrotalcite powder (manufacturer: SASOL GmbH Germany, product name: PURAL® MG70, MgO:Al$_2$O$_3$=70:30 (wt:wt)) was used. Calcination was performed in the same manner as that of Example 1, thereby preparing magnesium aluminate which is a catalyst for dehydration of a primary alcohol.

Examples 4 to 7

The magnesium aluminate prepared in Example 1 was used as a carrier, and a catalyst for dehydration of a primary alcohol was prepared, the catalyst supporting 1.0, 2.5, 5.0, or 7.5 wt % (W content) of tungsten.

Specifically, ammonium metatungstate (0.086 g, 0.22 g, 0.43 g, or 0.65 g) was added into 10 mL distilled water, and the magnesium aluminate (9.9 g, 9.75 g, 9.5 g, or 9.25 g) prepared in Example 1 was added thereto, so that a content of each tungsten (W) satisfies the above wt % with respect to the total weight of the catalyst. Mixing of the ammonium metatungstate and magnesium aluminate was performed for 60 minutes, and the mixture was calcined in an oven of 500° C. in an air atmosphere for 4 hours, thereby preparing a catalyst for dehydration of a primary alcohol, the catalyst supporting tungsten.

Example 8

The dehydration was performed by using the magnesium aluminate (MgAl$_2$O$_4$, MgO:Al$_2$O$_3$=30:70) prepared in Example 1.

Specifically, the dehydration was performed in a quartz reactor having a diameter of ⅜ inch and filled with the magnesium aluminate at a height of 0.75 cm. In order for complete vaporization of 1-octanol (99%, Sigma-Aldrich Corporation) which is a reactant, heating was performed by a preheater, and the dehydration was performed at a liquid hourly space velocity of 7 h$^{-1}$ and 400° C. using an HPLC pump.

The product produced by the dehydration was analyzed by a GC-FID (7890B, Agilent Technologies, Inc.) equipped with an HP-5 column (19091)-413, Agilent Technologies, Inc.). At this time, measurement times of the product were compared based on 3 hours of dehydration. In addition, the results thereof are shown in Table 1.

Examples 9 to 14

Dehydration was performed in the same manner as that of Example 8, except that the catalyst prepared in Examples 2 to 7 was used instead of the magnesium aluminate prepared in Example 1.

In Example 9, the catalyst prepared in Example 2 was used.

In Example 10, the catalyst prepared in Example 3 was used.

In Example 11, the catalyst prepared in Example 4 was used.

In Example 12, the catalyst prepared in Example 5 was used.

In Example 13, the catalyst prepared in Example 6 was used.

In Example 14, the catalyst prepared in Example 7 was used.

The product produced by the dehydration was also analyzed in the same manner as that of Example 8. In addition, the results thereof are shown in Table 1.

Examples 15 and 16

Dehydration was performed in the same manner as that of Example 8, except that a liquid hourly space velocity and a catalyst were adjusted as shown in Table 2.

The product produced by the dehydration was also analyzed in the same manner as that of Example 8. In addition, the results thereof are shown in Table 2.

Example 17

Dehydration was performed in the same manner as that of Example 8, except that hydrotalcite (manufacturer: SASOL GmbH Germany, product name: PURAL® MG30, MgO: $Al_2O_3$=30:70 (wt:wt)) was used as a catalyst instead of the magnesium aluminate ($MgAl_2O_4$).

The product produced by the dehydration was also analyzed in the same manner as that of Example 8.

Comparative Example 1

Dehydration was performed in the same manner as that of Example 8, except that a commercial alumina (manufacturer: SASOL GmbH Germany, $Al_2O_3$) was used as a catalyst instead of the magnesium aluminate.

The product produced by the dehydration was analyzed in the same manner as that of Example 8. In addition, the results thereof are shown in Table 1.

Comparative Example 2

Dehydration was performed in the same manner as that of Example 8, except that a commercial magnesium oxide (manufacturer: Sigma-Aldrich Corporation, MgO) was used as a catalyst instead of the magnesium aluminate.

The product produced by the dehydration was analyzed in the same manner as that of Example 8. In addition, the results thereof are shown in Table 1.

Comparative Example 3

Dehydration was performed in the same manner as that of Example 8, except that a mixture in which a commercial alumina (manufacturer: SASOL GmbH Germany, $Al_2O_3$) and a commercial magnesium oxide (manufacturer: Sigma-Aldrich Corporation, MgO) were mixed at a weight ratio of 70:30 was used as a catalyst instead of the magnesium aluminate.

The product produced by the dehydration was analyzed in the same manner as that of Example 8. In addition, the results thereof are shown in Table 1.

Comparative Examples 4 and 5

Dehydration was performed in the same manner as that of Example 8, except that a liquid hourly space velocity and a catalyst were adjusted as shown in Table 2.

The product produced by the dehydration was also analyzed in the same manner as that of Example 8. In addition, the results thereof are shown in Table 2.

TABLE 1

| (Catalyst) | Content of tungsten (wt %) | Conversion ratio of 1-octanol (%) | Selectivity for 1-octene (%) | Yield of 1-octene (%) | Purity of 1-octene (%) | Selectivity for dioctyl ether (%) |
|---|---|---|---|---|---|---|
| Example 8 | 0 | 75.1 | 81.7 | 61.3 | 89.6 | 8.8 |
| Example 11 | 1.0 | 71.7 | 77.4 | 55.5 | 86.5 | 11.1 |
| Example 12 | 2.5 | 72.3 | 75.9 | 45.3 | 89.2 | 14.9 |
| Example 13 | 5.0 | 82.4 | 79.5 | 65.5 | 84.6 | 5.9 |
| Example 14 | 7.5 | 72.0 | 70.8 | 48.9 | 73.2 | 7.1 |
| Comparative Example 1 ($Al_2O_3$) | — | 93.0 | 18.8 | 17.5 | 19.0 | 1.3 |
| Comparative Example 2 (MgO) | — | 4.8 | 10.6 | 0.5 | 100 | 89.4 |
| Comparative Example 3 ($Al_2O_3$ + MgO) | — | 94.4 | 29.2 | 27.6 | 29.5 | 1.0 |

* Dehydration conditions: reaction temperature (400° C.), liquid hourly space velocity (7 $h^{-1}$)

As shown in Table 1, it was confirmed that, in the case where the catalyst according to the present invention was used, the selectivity for 1-octene and the yield of 1-octene with respect to the dehydration of the primary alcohol were significantly excellent. Specifically, it was confirmed that the yield of 1-octene was significantly improved in Example 8 from the fact that the selectivity for 1-octene in Example 8 was up to 770% or more of the selectivity for 1-octene in Comparative Example 2.

In addition, it was confirmed that, in the case where the catalyst according to the present invention was used, the conversion ratio of 1-octanol was 70% or more, and the production of isomers was effectively suppressed, such that the selectivity for 1-octene which is a product finally produced from the dehydration was very high.

On the other hand, it was confirmed that, in Comparative Example 2 in which the catalyst having the lowest Lewis acid site intensity was used, the lowest conversion ratio of 1-octanol was exhibited, and the dioctyl ether was mainly produced, and thus the catalyst of Comparative Example 2 was not suitable for producing a linear alpha-olefin. On the contrary, it was confirmed that, in Comparative Example 1 in which the catalyst having the highest Lewis acid site intensity was used, the conversion ratio of 1-octanol was high, but the selectivity for 1-octene and the yield of 1-octene were low, and the purity of 1-octene which is a product finally produced was significantly low because the isomers excessively produced were not easily separated, and thus the catalyst of Comparative Example 1 was not suitable for producing a linear alpha-olefin.

TABLE 2

| (Sample No.) | Catalyst | Conversion ratio of 1-octanol (%) | Selectivity for 1-octene (%) | Yield of 1-octene (%) | Purity of 1-octene (%) | Selectivity for dioctyl ether (%) |
|---|---|---|---|---|---|---|
| Example 15 (Sample 3) | Example 1 (MgAl$_2$O$_4$, W: 0 wt %) | 61.5 | 80.0 | 49.2 | 93.7 | 14.6 |
| Example 16 (Sample 6) | Example 6 (MgAl$_2$O$_4$, W: 5.0 wt %) | 65.7 | 81.0 | 53.2 | 92.9 | 12.8 |
| Comparative Example 4 (Sample 2) | MgO | 0.2 | 0.0 | 0.0 | 0.0 | 100 |
| Comparative Example 5 (Sample 1) | Al$_2$O$_3$ | 98.3 | 26.5 | 26.0 | 26.6 | 0.2 |

* Dehydration conditions: reaction temperature (400° C.), liquid hourly space velocity (14 h$^{-1}$)

As shown in Table 2 and FIG. 1, it was confirmed that, in the case where the catalyst according to the present invention was used to increase the liquid hourly space velocity, 1-octene was selectively produced, the production of the isomers was effectively suppressed, and the selectivity for dioctyl ether having a significant boiling point difference was increased, and thus 1-octene with an excellent high purity was produced. Therefore, according to the present invention, the linear alpha-olefin was selectively produced with a high conversion ratio, and the selectivity for the product produced by the dehydration of the primary alcohol was easily controlled, such that a desired linear alpha-olefin with high purity may be produced.

According to the present invention, it is possible to provide a heterogeneous catalyst or a catalyst system that has an excellent catalyst stability while having an excellent catalytic activity with respect to dehydration of a primary alcohol, and a high turnover frequency. Further, in the case of the catalyst according to the present invention, high catalytic activity may be implemented with a relatively small amount of a catalyst as compared with a liquid phase homogeneous catalyst system.

Further, according to the present invention, by adequately controlling a Lewis acid site, the production of isomers may be effectively suppressed, and both high purity and high conversion ratio may be implemented during the dehydration of the primary alcohol.

Further, according to the present invention, a primary alcohol may be converted into an olefin with a high selectivity, and a linear alpha-olefin may be produced with a high yield, and thus the linear alpha-olefin may be mass-produced by a very cost-effective method. Further, by using a solid phase catalyst or catalyst system, a liquid phase reactant and a product are easily separated from each other.

It will be obvious to those skilled in the art to which the present invention pertains that the present invention described above is not limited to the above-mentioned exemplary embodiments and the accompanying drawings, but may be variously substituted, modified, and altered without departing from the scope and spirit of the present invention.

What is claimed is:

1. A method of converting a primary alcohol into an olefin, the method comprising:
    converting the primary alcohol into the olefin by contacting the primary alcohol with a catalyst for dehydration of the primary alcohol, the catalyst comprising a carrier of magnesium aluminate, hydrotalcite, or a combination thereof, and Group VI transition metal particles supported on the carder.
2. The method of claim 1, wherein the Group VI transition metal particles are formed of tungsten.
3. The method of claim 1, wherein the Group VI transition metal particles are supported in an amount of 10 wt % or less with respect to a total weight of the carrier.
4. The method of claim 1, wherein the primary alcohol is 1-octanol.
5. The of method claim 1, further comprising preparing the catalyst for dehydration of the primary alcohol by the following steps:
    impregnating the carrier with a precursor solution of the Group VI transition metal particles; and
    calcining the impregnated carrier.
6. The method of claim 5, wherein the Group VI transition metal precursor of the metal precursor solution is an ammonium-based compound.
7. The method of claim 5, wherein the Group VI transition metal precursor is ammonium paratungstate, ammonium metatungstate, or a combination thereof.
8. A method of producing a linear alpha-olefin, the method comprising:
    converting a primary alcohol into a converted product comprising the linear alpha-olefin by contacting the primary alcohol with a catalyst for dehydration of the primary alcohol, the catalyst comprising magnesium aluminate, hydrotalcite, or a combination thereof as a carrier, and Group VI transition metal particles supported on the carrier;
    fractionating the converted product; and
    recovering the linear alpha-olefin.
9. The method of claim 8, wherein the converting is performed at 200 to 800° C.
10. The method of claim 8, wherein, in the converting, the primary alcohol is fed at a liquid hourly space velocity of 3 to 100 h$^{-1}$.
11. The method of claim 8, wherein the fractionating is performed by distillation, extraction, adsorption, or ion exchange.
12. The method of claim 8, wherein a conversion ratio of the primary alcohol is 50% or more, and a selectivity for the linear alpha-olefin is 60% or more.

* * * * *